US010246427B2

(12) United States Patent
Szafranski et al.

(10) Patent No.: US 10,246,427 B2
(45) Date of Patent: Apr. 2, 2019

(54) DERIVATIVES OF 1,2,3-TRIAZOLYL CYCLOHEXAN-1-OL AND ITS USE

(71) Applicant: UNIWERSYTET JAGIELLONSKI, Cracow (PL)

(72) Inventors: Przemyslaw Szafranski, Chorzow (PL); Patryk Kasza, Tychy (PL); Marek Cegla, Cracow (PL)

(73) Assignee: UNIWERSYTET JAGIELLONSKI, Crakow (PL)

( * ) Notice: Subject to any disclaimer, the term of this patent is extended or adjusted under 35 U.S.C. 154(b) by 0 days.

(21) Appl. No.: 15/580,040

(22) PCT Filed: Jun. 7, 2016

(86) PCT No.: PCT/PL2016/050026
§ 371 (c)(1),
(2) Date: Dec. 6, 2017

(87) PCT Pub. No.: WO2016/200283
PCT Pub. Date: Dec. 15, 2016

(65) Prior Publication Data
US 2018/0297960 A1 Oct. 18, 2018

(30) Foreign Application Priority Data

Jun. 8, 2015 (PL) .......................... 412594

(51) Int. Cl.
C07D 401/06 (2006.01)
C07D 249/04 (2006.01)
C07D 405/04 (2006.01)

(52) U.S. Cl.
CPC ......... C07D 249/04 (2013.01); C07D 401/06 (2013.01); C07D 405/04 (2013.01)

(58) Field of Classification Search
CPC ..................... C07D 401/06; C07D 249/04
See application file for complete search history.

(56) References Cited

U.S. PATENT DOCUMENTS

| 7,375,234 | B2 | 5/2008 | Sharpless et al. | 548/255 |
| 7,763,736 | B2 | 7/2010 | Sharpless et al. | 548/255 |
| 2015/0031895 | A1 | 1/2015 | Sharpless et al. | 548/255 |

FOREIGN PATENT DOCUMENTS

| KR | 10-2009-0124613 | 12/2009 | ............ C01D 249/02 |
| WO | WO 2009/038685 A1 | 3/2009 | ............ A01N 43/64 |
| WO | WO 2011/019799 A2 | 2/2011 | ............ C07D 249/04 |
| WO | WO 2012/021390 A1 | 2/2012 | ............ G01N 33/53 |

OTHER PUBLICATIONS

Chemical Abstracts Registry No. 1351677-98-9, indexed in the Registry file on STN CAS Online Dec. 22, 2011 (Year: 2011).*
Chemical Abstracts Registry No. 1234258-73-6, indexed in the Registry file on STN CAS Online Jul. 29, 2010. (Year: 2010).*
Chemical Abstracts Registry No. 1817837-32-3, indexed in the Registry file on STN CAS Online Nov. 4, 2015. (Year: 2015).*
Hatit et al., Organic Letters, 18(17), pp. 1694-1697, published online Mar. 22, 2016, and Supporting Information, pp. 1-32. (Year: 2016).*
Szafranski et al., Tetrahedron Letters, 56(45), published online Sep. 26, 2015, pp. 6244-6247. (Year: 2015).*
Binder et al.; 'Click' Chemistry in Polymer and Materials Science; Macromol. Rapid Commun. 28 (2007) 15-54. doi: 10.1002/marc. 200600625 (The year of publication is sufficiently earlier than the effective U.S. filed and any foreign priority so that the particular month of publication is not in issue).
Binder et al; 'Click Chemistry in Polymer and Materials Science: An Update; Macromol. Rapid Commun. 29 (2008) 952-981 (http://onlinelibrary.wiley.com/doi/10.1002/marc.2008/00089/full (The year of publication is sufficiently earlier than the effective U.S. filing date and any foreign priority so that the particular month of publication is not in issue).
Bock et al.; $Cu^1$-Catalywd Alkyne-Azide "Click" Cycloadditions from a Mechanistic and Synthetic Perspective; European J. Org. Chem.; (2006) 51-68; doi:10.1002/ejoc.200500483 (The year of publication is sufficiently earlier than the effective U.S. filing date and any foreign priority so that the particular month of publication is not in issue).
Boren et al,; Ruthenium-catalyzed azide-alkyne cycloaddition: scope and mechanism; J. Am. Chem. Soc.; 130 (2008)'8923-30; doi:10. 1021/ja0749993 (The year of publication is sufficiently earlier than the effective U.S. filing date and any foreign priority so that the particular month of publication is not in issue).
Chan et al.; Polytriazoles as copper(I)-stabilizing ligands in catalysis; Org. Lett. 6 (2004); 2853-5; doi:10.1021/ol0493094 (The year of publication is sufficiently earlier than the effective U.S. filing date and any foreign priority so that the particular month of publication is not in issue).
Diez-Gonzalez et al.; [(NHC)$_2$Cu]X complexes as efficient catalysts for azide-alkyne click chemistry at low catalyst loadings; Angew. Chemie—Int. Ed. 47 (2008) 120; 9013-9016. doi:10.1002/ange. 200803289 (The year of publication is sufficiently earlier than the effective U.S. filing date and any foreign priority so that the particular month of publication is not in issue).
Diez-Gonzalez et al.; (NHC)copper(I)-catalyzed [3+2] cycloaddition of asides and Mono- or disubstituted alkynes; Chem.—A Eur. J. 12 (2006); 7558-7564. doi:10.1002/chem.200600961 (The year of publication is sufficiently earlier than the effective U.S. filing date and any foreign priority so that the particular month of publication is not in issue).

(Continued)

Primary Examiner — Laura L Stockton
(74) Attorney, Agent, or Firm — Renner Kenner Greive Bobak Taylor & Weber

(57) ABSTRACT 1,2,3-triazolyl cyclohexanol derivatives have been disclosed and their use as ligands accelerating the copper(I)-catalyzed azide-alkyne cycloaddition and the zinc(II)-catalyzed azide-nitrile cycloaddition.

6 Claims, 2 Drawing Sheets

(56) References Cited

OTHER PUBLICATIONS

Diez-Gonzalez et al.; *Well-defined copper(i) complexes for Click azide-alkyne cycloaddition reactions: one Click beyond*; Catal. Sci. Technol. 1 (2011); 166, doi:10.1039/c0cy00064g (The year of publication is sufficiently earlier than the effective U.S. filing date and any foreign priority so that the particular month of publication is not in issue).

Diez-Gonzalez et al.; *[(NHC)CuCl] complex as a latent Click catalyst*: Chem. Commun. (Camb): (2008) 4747-4749; doi:10.1039/b806806b (The year of publication is sufficiently earlier than the effective U.S. filing date and any foreign priority so that the particular month of publication is not in issue).

Golas et al.; *Catalyst Performance in "Click" Coupling Reactions of Polymers Prepared by ATRP: Ligand and Metal Effects*; Macromolecules. 39; (Aug. 2006) 6451-6457; doi: 10.1021/ma061592u.

Gonda et al.; *Highly active copper-catalysts for azide-alkyne cycloaddition*; Dalton Trans. 39; (Oct. 2009) 726-729; doi:10.1039/b920790m.

Hathaway; *An Aldol Condensation Experiment Using a Number of Aldehydes and Ketones*; Journal of Chemical Education; vol. 64, No. 4; Apr. 1987; pp. 367-368.

C. Hein et al.; *Click chemistry, a powerful tool for pharmaceutical sciences*; Pharm. Res. 25; (May 2008) 2216-30; doi:10.1007/s11095-008-9616-1.

J. Hein et al.; *Copper-catalyzed azide-alkyne cycloaddition (CuAAC) and beyond: new reactivity of copper(I) acetylides*; Chem. Soc. Rev.; 39 (Mar. 2010); 1302-1315; doi:10.1039/b904091a.

Ogata et al.; *2-Ethynylpyridine-Promoted Rapid Copper(I) Chloride Catalyzed Aside-Alkyne Cycloacidition Reaction in Water*; Synlett. 24; (Mar. 2013); 843-846; doi:10.1055/s-0032-1318488.

Huisgen; *Kinetics and Mechanism of 1,3-Dipolr Cycloadditions*: Angew. Chemie Int. Ed. English; vol. 2 (Nov. 1963); 633-645; doi:10.1002/anie,196306331.

Huisgen; *1,3-Dipolar Cycloadditions. Past and Future*; Angew. Chemie Int. Ed. English; vol. 2; (Oct. 1963); 565-598; doi:10.1002/anie.196305651.

Kaur et al.; *(NHC) Cu$^1$ (NHC=N-Heterocyclic carbene) complexes as efficient catalyst for the reduction of carbonyl compounds*; Organometallics 23; (Feb. 2004) 1157-1160; doi:10.1021/om034285a.

Kolb et al.; *Click Chemistry: Diverse Chemical Function from a Few Good Reactions*; Angew. Chem. Int. Ed. Eng.; vol. 40; (2001) 2004-2021; http://www.ncbi.nlm.nih.gov/pubmed/11433435 ((The year of publication is sufficiently earlier than the effective U.S. filing date and any foreign priority so that the particular month of publication is not in issue)).

Kolb et al.; *The growing impact of click chemistry on drug discovery*; Drug Discov. Today; vol. 8; (Dec. 2003) 1128-1137; doi:10.1016/S1359-6446(03)02933-7.

Lange et al.; *Keynote review: Medicinal chemistry strategies to CBI cannabinoid receptor antagonists*; Drug Discov. Today. 10 (May 2005) 693-702. doi:10.1016/S1359-6446(05)03427-6.

Malkoch et al.; *Structurally Diverse Dendritic Libraries; A Highly Efficient Functionalization Approach Using Click Chemistry*; Macromolecules; 38 (Apr. 2005) 3663-3678. doi:doi:10.1021/ma047657f.

Meldal et al: *Cu-catalyzed azide-alkyne cycloaddition*; Chem. Rev; 108; (Aug. 2008) 2952-3015; doi:10.1021/cr0783479.

Michael; *About acting of diazobenzolimide on acetylenedicarboxylic acid methyl ester*; J. Für Prakt. Chemie,; 48 (Jun. 1893) 94-95.

Ozcubukcu et al,; *A highly active catalyst for Huisgen 1,3-dipolar cycloadditions based on the tris(triazolyl)methanol-Cu(I) structure*; Org. Lett. 11; (Sep. 2009) 4680-3; doi:10.1021/ol9018776.

Ozkal et.al.; *Covalently immobilized tris(triazolyl)methanol—Cu(i) complexes: highly active and recyclable catalysts for CuAAC reactions*; Catal. Sci. Technol; 2 (2012); 195; doi:10.1039/c1cy00297j (The year of publication is sufficiently earlier than the effective U.S. filing date and any foreign priority so that the particular month of publication is not in issue).

Pearson; *Electronic spectra and chemical reactivity*; J. Am. Chem. Soc.; 110 (1988); 2092-2097; doi:10.1021/ja00215a013 (The year of publication is sufficiently earlier than the effective U.S. filing date and any foreign priority so that the particular month of publication is not in issue).

Perez-Balderas et al.; *Multivalent neoglycoconjugates by regiospecific cycloaddition of alkynes and azides using organic-soluble copper catalysts*; Org. Lett. 5; (May 2003) 1951-1954; doi:10.1021/ol034534r.

Rostovtsev et al.; *A Stepwise Huisgen Cycloaddition Process: Copper(I)-Catalyzed Regioselective "Ligation" of Azides and Terminal Alkynes*; Angew. Chemie; 114 (2002); 2708-2711; doi:10.1002/1521-3757(Jul. 15, 2002)114:14<2708::AID-ANGE2708>3.0.CO;2-0 (The year of publication is sufficiently earlier than the effective U.S. filing date and any foreign priority so that the particular month of publication is not in issue).

Thirumurugan et al.; *Click chemistry for drug development and diverse chemical-biology applications*: Chem. Rev.; 113 (2013); 4905-79; doi:10.1021/cr200409f (The year of publication is sufficiently earlier than the effective U.S. filing date and any foreign priority so that the particular month of publication is not in issue).

Tornoe et al; *Peptidotrictzoles: Copper(1)-catalyzed 1, 3-dipolar cycloadditions on solid-phase, in: Pept. Wave Futur. Proc. Second Int. Seventeenth Am. Pept. Symp.* Jun. 9-14, 2001. San Diego, California, U.S.A., 2001: pp. 3057-3064. http://link.springer.com/chapter/10.1007/978-94-010-0464-0_119 (accessed Dec. 30, 2014).

Tornoe et al.; *Peptidotrtazoles on Solid Phase*: [1,2,3]-*Triazoles by Regiospectfic Copper(I)-Catalyzed 1,3-Dipolar Cycloadditions of Terminal Alkynes to Azides*; J. Org. Chem.; 67 (Apr. 2002); 3057-3064; doi:10.1021/jo011148j.

Tron et al.; *Click chemistry reactions in medicinal chemistry: applications of the 1,3-dipolar cycloaddition between azides and alkynes*: Med. Res. Rev. 28; (Aug. 2007) 278-308; doi:10.1002./med.20107.

Wu et al., *Efficiency and fidelity in a click-chemistry route to triazole dendrimers by the copper(I)-catalyzed ligation of azides and alkynes*; Angew. Chemie—Int. Ed; 43 (2004); 3928-3932; doi:10.1002/anie.200454078 (The year of publication is sufficiently earlier than the effective U.S. filing date and any foreign priority so that the particular month of publication is not in issue), pp. 4018-4022.

Zhang et al; *Ruthenium-catalyzed cycloaddition of alkynes and organic azides*; J. Am. Chem. Soc.; 127; (2005) 15998-9; doi:10.1021/ja054114s (The year of publication is sufficiently earlier than the effective U.S. filing date and any foreign priority so that the particular month of publication is not in issue).

Database Registry; *Chemical Abstracts Service*; Columbus Ohio, US; Dec. 20, 2013; XP002760498; database accession No. 1499628-29-3.

Acquaah-Harrison et al.; *Library of 1,4-Disubstituted 1,2,3-Triazole Analogs of Exazolidinone RNA-Binding Agents*: Journal of Combinaorial Chemistry; vol. 12, No. 4; Jul. 12, 2010; pp. 491-496.

Zhou et al.; *Anisotropy studies of tRNA-T box antiterminator RNA complex in the presence of 1,4-disubstituted 1,2,3-triazoles*; Bioorganic & Medicinal Chemistry Letters; Pergamon, Amsterdam, NL; vol. 21, No. 23; Sep. 22, 2011; pp. 7059-7063.

International Search Report dated Aug. 18, 2016 in related application No. PCT/PL2016/050026.

Written Opinion dated Aug. 18, 2016 in related application No. PCT/PL2016/050026.

\* cited by examiner

DERIVATIVES OF 1,2,3-TRIAZOLYL CYCLOHEXAN-1-OL AND ITS USE

CROSS-REFERENCE TO RELATED APPLICATION

This is a § 371 application of International Patent Application No. PCT/PL2016/050026, filed Jun. 7, 2016, which claims benefit of Polish Patent Application No. P.412594, filed Jun. 8, 2015, and which is incorporated herein by reference.

TECHNICAL FIELD

The invention concerns novel 1,2,3-triazolyl cyclohexan-1-ol derivatives and their use as ligands in copper(I)-catalyzed azide-alkyne cycloaddition (catalyzed variant of the Huisgen reaction) and zinc(II)-catalyzed azide—nitrile cycloaddition.

BACKGROUND OF INVENTION

Presently, the Huisgen cycloaddition reaction is one of the most widely-known 3+2 cycloaddition reactions. First mentions of this reaction come from the works of Michael at the end of the $19^{th}$ century[1] and the most important advances in the uncatalyzed variant of this reaction were brought by the work of R. Huisgen in the second half of the $20^{th}$ century [2,3]. The beginning of the $21^{st}$ century brought rapid development in the field thanks to the catalytic variants of the reaction using copper(I) (CuAAC) [4-7] and ruthenium (II) (RuAAC) [8,9]. Compared to the uncatalyzed variant, they allow to regioselectively obtain 1,4- and 1,5-disubstituted 1,2,3-triazoles (Scheme 1).

Scheme 1: Azide-alkyne cycloaddition reactions

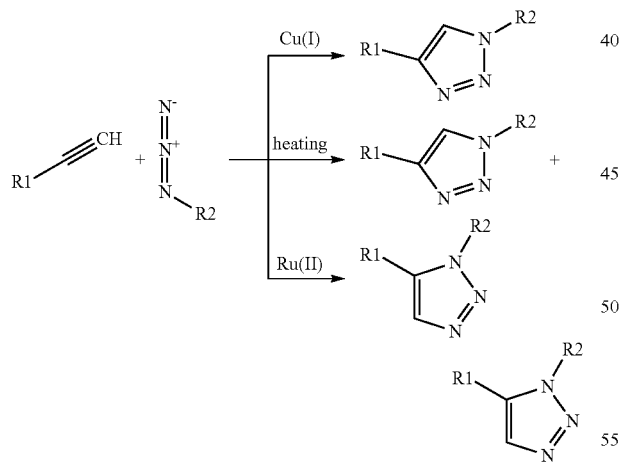

Thanks to its regioselectivity and high yields, the catalyzed Huisgen cycloaddition variants found a broad range of uses in multiple fields of chemistry and related disciplines. The applications of the cycloaddition reaction include the synthesis of novel biologically active compounds or tagging of biomolecules or even whole cells/cell fragments in living systems. A more detailed description of these uses can be found in a number of review articles concerning biological chemistry, pharmacy and drug design [10-14], as well as materials science and polymer research [15,16].

In 2001, Sharpless[4,6] and Meldal [5,17] independently showed that copper(I) ions catalyze the Huisgen cycloaddition reaction. This discovery together with the "Click chemistry" concept, presented by K. B. Sharpless [4] initiated rapid growth of interest in this reaction in recent years.

This allowed to identify a number of problems and limitations of these reactions as well as to develop a number of advanced variants overcoming these limitations [18]. One of these solutions is use of ligands complexing copper(I) ions to increase the efficacy of the reaction.

The U.S. Pat. No. 7,375,234 patent concerns the copper(I) catalyzed cycloaddition of azides and alkynes (further abbreviated CuAAC). A cycloaddition process was revealed, not including the addition of an amine or a ligand.

The U.S. Pat. No. 7,763,736 B2 patent discloses a reaction proceeding in an aqueous solution of an alcohol and use of amine or ligand such as e. g. TBTA.

A number of ligands used for the CuAAC reaction are also known. These ligands can be divided into two categories, depending on the chemical nature of metal-interacting electron pairs. These are the "hard" and "soft" ligands. [19,20] Cu(I) is considered a "marginally weak" Lewis acid.[21]

The "soft" ligands include phosphines containing a single bond coordinating to the Cu atom. Examples of these are $Cu(P(OMe_3)_3Br,[22]$ $(EtO)_3PCuI$ [22] and $Cu(PPh_3)_3Br$. [23,24] The mentioned complexes are most commonly used when the insolubility of Cu(I) species becomes a significant problem. For CuAAC reactions performed in toluene and dichloromethane, bis(phosphine) complexes like Cu $(PPh_3)_2OAc$ are efficient.[25]

Information concerning the use of Cu(I) complexes with N-heterocyclic carbene (NHC) ligands in CuAAC have been disclosed.[26,27] The copper concentrations used for these reactions can be reduced to ppm level.[28] The most-often used NHC ligands are [(SiMes)CuBr][29] and [(SiPr)Cu Cl].[30]

The "hard" ligands have been dominated by amines and it is the nitrogen atom-based structure that is dominant within the CuAAC ligands.[31] The most important catalytic ligand for CuAAC is TBTA [32] (Scheme 2, below). Due to the poor aqueous solubility of TBTA, water-soluble ligands such as THPTA have been designed, including polar substituents aimed to increase the ligand's solubility in aqueous media.

Scheme 2: The structures of amine ligands used for CuAAC reactions

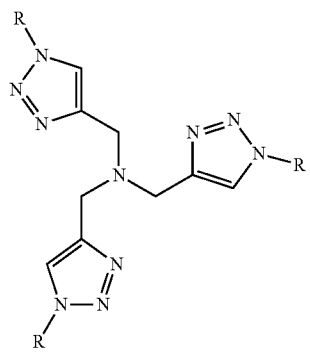

10a-b a) R = benzyl (TBTA)
b) R = tert-butyl (TTTA)

-continued 11a-c a) R = CH₂CH₂CH₂OH (THPTA)
b) R = CH₂CH₂CO₂H
c) R = CH₂C₆H₄CO₂H

12

13a, b a) R = H
b) R = Et

Among the "hard" N-donor ligands, tris(triazolyl)methanol derivatives [33,34] should also be mentioned, as well as 4-(2-pyridil)-1,2,3-triazole, proposed by Fukuzawa et all. [35], and the concept of using 2-ethynylpyridine as a reaction-accelerating additive (In situ generated catalytic ligand).

Further cycloaddition ligands and their uses have been disclosed in patent applications published as WO2012021390 and WO2009038685.

Three fundamental types of technical problems with the present 3+2 cycloaddition ligands can be distinguished. The first one is limited efficacy of the known aromatic ligands for aliphatic substrates.

Second problem is the difficulty in removing the catalytic ligand from the reaction product.

The third one is limited number and relative complexity of the known water-soluble CuAAC ligands.

Unexpectedly, the abovementioned problems have found solution in the subject invention.

SUMMARY OF INVENTION

The subject of the invention is a chemical compound and its use (see FIG. 1) described in the appended patent claims.

BEST MODE FOR CARRYING OUT THE INVENTION

Figure 1:
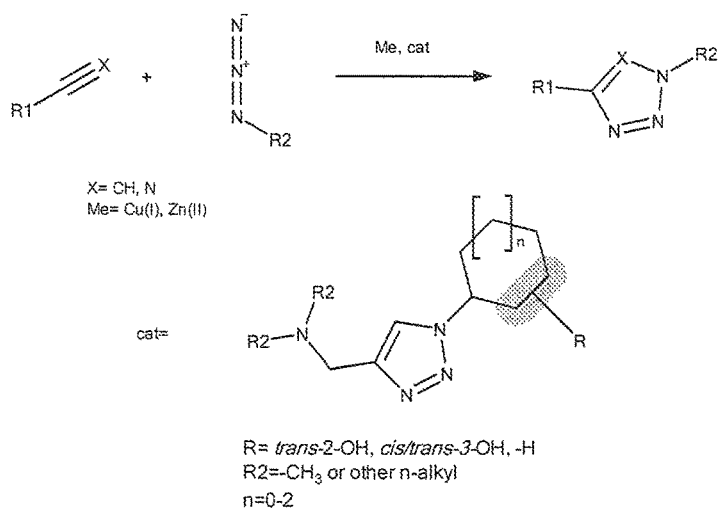
FIG. 1 is a representative schematic drawing of the chemical reaction producing the chemical compound of the present invention.

In a particular realization the presented invention concerns a novel chelate ligand, 2-{4-[(dimethylamino)methyl]-1,2,3-triazolyl}cyclohexan-1-ol (further abbreviated AMTC), which allows to obtain higher yields of CuAAC reactions and higher product purities for aliphatic substrates.

AMTC displays a visible selectivity towards aliphatic substrate sets, in comparison to aromatic substrate sets, for which TBTA is most efficient.

Aqueous solubility of the presented ligand allows to easily remove it from reaction mixtures through extraction. This allows to obtain higher purity products.

Thanks to its simple structure and molecular mass lower than that of the known ligands, AMTC is a viable alternative to the known lignads.

The compound of the general formula:

wherein:
substituents in the aliphatic ring are in cis- or trans-relative configuration, and
$R_1$ is one of the following substituents: —H, =O, —OH, —OCH₃, —NH₂, —N(CH₃)₂, —NHCH₃ —SH, —SCH₃
$R_2$ is one of the following substituents: —H, =O, —OH, —OCH₃, —NH₂, —N(CH₃)₂, —NHCH₃ —SH, —SCH₃
$n$ is an integer from 0 to 3
$R_3$ is an alkyl chain containing 1-3 carbon atoms, especially methyl $R_4$ is an alkyl chain containing 1-3 carbon atoms, especially methyl
or
substituents in the aliphatic ring are in cis- or trans-relative configuration, and
$R_1$ is one of the following substituents: —H, =O, —OH, —OCH$_3$, —NH$_2$, —N(CH$_3$)$_2$, —NHCH$_3$ —SH, —SCH$_3$
$R_2$ is one of the following substituents: —H, =O, —OH, —OCH$_3$, —NH$_2$, —N(CH$_3$)$_2$, —NHCH$_3$ —SH, —SCH$_3$
n is an integer from 0 to 3
and $R_3$ and $R_4$ together with the nitrogen atom form one of the systems presented below:

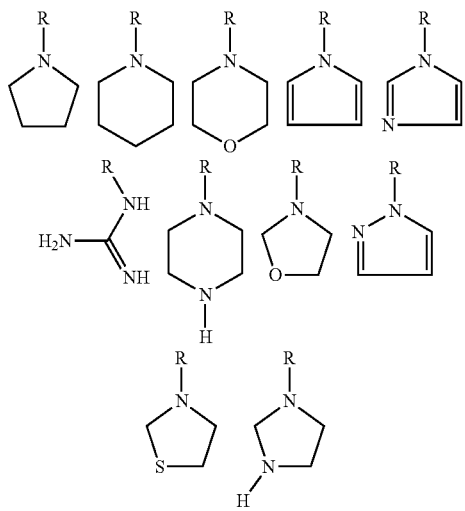

wherein R is the remaining part of the molecule described above.

The examples presented below describe the structure and synthesis of AMTC and its analogs as well as examples of their use in CuAAC reactions, proving the efficacy of the invention.

AMTC was obtained in a copper-catalyzed cycloaddition of trans-2-azidocyclohexan-1-ol and N,N-dimethylpropargylamine in water, using the CuSO$_4$—sodium ascorbate catalytic system applied in various amounts. The reaction product was isolated by extraction with an organic solvent (dichloromethane) from an alkaline aqueous solution and next, it was purified through hydrobromide crystallization if necessary (EXAMPLE 1).

Example 1. 2-{4-[(dimethylamino)methyl]-1,2,3-triazolyl}cyclohexan-1-ol 0.38 g of trans-2-azidocyclohexan-1-ol was suspended in 2 mL of water and 1.1 mL of DMF was added. Next, the mixture was transferred to a flask containing 0.2 g of N,N-dimethylpropargylamine. Next, 60 mg (10 mol %) of CuSO$_4$*5H$_2$O was added, dissolved in 2 mL of water, followed by 4 mL of water. The reaction was initiated by adding 47 mg (10 mol %) of sodium ascorbate dissolved in 2 mL of water. The reaction mixture was stirred overnight at room temperature. After the stirring was finished, 15 mL of 10% aqueous NaOH was added and the mixture was extracted with 5×15 mL of dichloromethane. The combined organic layers were washed with 2×15 mL of 10% aqueous NaOH, dried over MgSO$_4$ and evaporated under reduced pressure. The procedure yielded 0.55 g of an oily crude product which was analyzed by $^1$H NMR.

0.545 g of the crude product was dissolved in 6 mL of ethyl acetate at room temperature and 0.13 mL of 48% aqueous HBr was added. An oil precipitated, which crystallized upon cooling overnight at 0° C. The mass of the thus obtained hydrobromide was 389 mg.

The hydrobromide was separated by filtration and dried under reduced pressure, and next it was dissolved in a minimal amount of water followed by alkalization by adding 10 mL of 10% aqueous NaOH and extraction with 3×10 mL of dichloromethane. The combined organic layers were dried and evaporated under reduced pressure to yield 150 mg of the pure product.

Example 2. 2-{4-[(dimethylamino)methyl]-1,2,3-triazolyl}cyclohexan-1-ol 1.0 g of N,N-dimethylpropargylamine and 1.69 g of trans-2-azidocyclohexan-1-ol were dissolved in 12 mL of 0.05 mol/dm$^3$ CuSO$_4$, and 0.119 g of sodium ascorbate was added, dissolved in 3 mL of water. The reaction mixture was stirred at room temperature for 1.5 h. After the stirring was completed, 30 mL of 10% NaOH was added to the mixture, followed by extraction with 4×15 mL of dichloromethane. The combined organic layers were washed with 1×10 mL of 10% aqueous NaOH with several drops of 0.5% aqueous hydrogen peroxide and 1×15 mL of water, dried over anhydrous MgSO$_4$ and evaporated under reduced pressure to yield 1.64 g of the crude product which was further purified.

1.64 g of the crude product was dissolved in 18 mL of ethyl acetate and 0.64 mL of 48% aqueous HBr was added. The solution was left for crystallization at 0° C. Thus obtained hydrobromide was washed with a small amount of ethyl acetate, dried and weighed; its mass was 2.23 g. Next, the solid was dissolved in a minimal amount of water, followed by adding 50 mL of 10% aqueous NaOH and extraction with 3×20 mL of dichloromethane. The process yielded 1.039 g of the pure product.

Example 3. 2-{4-[(dimethylamino)methyl]-1,2,3-triazolyl}cyclohexan-1-ol 1.69 g of trans-2-azidocyclohexan-1-ol and 1.3 mL of N,N-dimethylpropargylamine were added to 7.5 mL of water, followed by 2.40 mL of 0.05 mol/dm$^3$ aqueous CuSO$_4$ (1 mol % Cu). Next, 24 mg of sodium ascorbate (0.12 mmol, 1 mol %), dissolved in 1 mL of water, was slowly added during intense stirring. The stirring was continued for 2 h at room temperature. After the reaction was finished, 30 mL of 40% aqueous NaOH was added and the mixture was extracted with 4×15 mL of dichloromethane. The combined organic layers were washed with 2×5 mL of 10 mg/mL aqueous EDTA solution, 2×5 mL of water and dried over anhydrous MgSO$_4$. Evaporation under reduced pressure yielded 2.48 g (92%) of a clear oil, which crystallized upon cooling.

Similar procedures may be used to obtain analogs of AMTC.

Example 4. 1-(trans-3-hydroxycyclohexyl)-4-[(dimethylamine)methyl]-1,2,3-triazole To 0.4 g of N,N-dimethylpropargylamine and 0.67 g of trans-3-azidocyclohexanol, 3.6 mL of 0.05 mol/dm$^3$ aqueous CuSO$_4$ was added, followed by 6 mL of water. After the water was added, 35 mg of sodium ascorbate was directly added and the reaction was stirred at room temperature for 1.5 h. After the stirring was completed, 15 mL of dichloromethane, 10 mL of 10% aqueous NaOH and 0.1 mL of 0.5% hydrogen peroxide were added and the organic layer was separated. The aqueous layer was extracted with 4×10 mL of dichloromethane. The combined organic layers were washed with 1×10 mL of 10% aqueous NaOH and 1×5 mL of water and dried over anhydrous $MgSO_4$. Evaporation under reduced pressure yielded 0.56 g of the crude product.

The crude product (0.56 g) was dissolved in 15 mL of ethyl acetate, 0.25 mL of 48% aqueous HBr was added and the mixture was left to crystallize at 0° C. The obtained precipitate was filtered, dried and weighed (m=0.675 g), and next, 8 mL of 10% aqueous NaOH was added, followed by extraction with 4×10 mL of dichloromethane. The combined organic layers were washed with 1×5 mL of water and dried over anhydrous $MgSO_4$. Evaporation under reduced pressure yielded 0.352 g of the pure product in the form of a white crystalline solid.

Example 5. 1-cyclohexyl-4-[(dimethylamine)methyl]-1,2,3-triazole

N,N-dimethylpropargylamine (0.75 g) and azidecyclohexane (1.05 g) were dissolved in 0.05 mol/dm$^3$ aqueous $CuSO_4$ (9 mL), followed by the addition of water (13 mL). Next, sodium ascorbate was added (89 mg) and the mixture was stirred at room temperature for 2 h. After the stirring was completed, several drops of 5% hydrogen peroxide, 10% aqueous NaOH (10 mL) and dichloromethane (15 mL) were added, and the organic layer was separated. The aqueous layer was extracted with dichloromethane (4×10 mL). The combined organic layers were washed with 10% aqueous NaOH (1×5 mL) and water (1×5 mL), followed by drying over anhydrous $MgSO_4$. Evaporation under reduced pressure yielded 1.44 of a solid product.

Example 6. Structural and Analytical Data

AMTC $^1$H NMR ($D_2O$, 300 MHz): δ=7.82 (s, 1H), 4.61-4.68 (m, 1H), 4.07-4.24 (m, 1H), 3.68-3.83 (m, 1H), 3.46 (s, 2H), 2.03 (s, 6H), 1.86-2.00 (m, 2H), 1.55-1.78 (m, 3H), 1.13-1.38 ppm (m, 3H)

$^{13}$C NMR ($D_2O$, 75 MHz): δ=142.7, 124.1, 72.3, 66.6, 52.0, 43.1, 33.7, 31.7, 24.1, 23.6 ppm IR (ATR/diament), pasma [cm$^{-1}$] (transmittance): 3153 (86%), 3057 (wide, 84%), 2935 (73%), 2845 (76%), 2782 (78%), 1551 (93%), 1462 (84%), 1080 (82%), 1024 (82%)

LC-MS

Analytical conditions: C-18 column in reversed-phase mode, water-acetonitrile gradient elution (linear gradient, 0-99% of acetonitrile during 10 min) with 0.1% HCOOH addition Retention time: 1.66 min M+1 value: 225.16

ES+ peaks (intensity): 225.09 (100%); 226.02 (~17%); 227.02 (~2%)

Elemental analysis. The results are given below (Table 1)

TABLE 1

Elemental analysis results for AMTC

|   | Experimental | Calculated |
|---|---|---|
| C | 59.24 ± 0.17 | 58.9% |
| N | 25.28 ± 0.11 | 24.98% |
| H | 6.774 ± 0.006 | 8.99% |
| S | 0.1795 ± 0.063 | 0.0% |

1-(trans-3-hydroxycyclohexyl)-4-[(dimethylamine)methyl]-1,2,3-triazole $^1$H NMR ($D_2O$, 300 MHz): δ=7.80 (s, 1H), 4.56-4.72 (m, 1H), 4.02-4.13 (m, 1H), 3.44 (s, 2H), 2.01 (s, 6H), 1.83-1.98 (m, 3H), 1.34-1.76 ppm (m, 5H)

$^{13}$C NMR ($D_2O$, 75 MHz): δ=142.7, 123.2, 66.0, 56.1, 51.9, 43.0, 38.2, 31.8, 30.5, 18.7 ppm 1-cyclohexyl-4-[(dimethylamine)methyl]-1,2,3-triazole $^1$H NMR ($D_2O$, 300 MHz): δ=7.81 (s, 1H), 4.33 (m, 1H), 3.49 (s, 2H), 2.05 (s, 6H), 1.90-2.02 (m, 2H), 1.64-1.79 (m, 2H), 1.58 (m, 3H), 1.30 (m, 2H), 1.13 ppm (m, 1H)

$^{13}$C NMR ($D_2O$, 75 MHz): δ=142.5, 123.1, 60.5, 51.9, 43.0, 32.8, 24.5 ppm

Example 7. AMTC Efficacy as a CuAAC Ligand

To confirm the efficacy of AMTC as a ligand accelerating the copper catalyzed Huisgen cycloaddition, a set of optimized synthetic procedures was developed, allowing to obtain pure products in high yields, with no need for additional purification. Next, the efficacy and substrate selectivity of AMTC were compared to a commonly used ligand—TBTA. The last part of the tests was a solvent composition study covering the efficacy of AMTC for selected substrate sets in various water-ethanol compositions.

a. Optimal Synthetic Procedures Using AMTC

To develop efficient cycloaddition procedures using AMTC, a typical synthetic procedure was investigated, using various concentrations of the copper(II)-ascorbate catalytic system, in various solvents. The water-ethanol mixture was selected as the best solvent, which enables to obtain high-purity products in good yields. The reactions in dichloromethane were efficient, but effected in the formation of considerable amounts of impurities difficult to remove, whereas the reactions in tetrahydrofurane gave poor yields and complex byproduct mixtures.

Optimized synthetic procedures were developed for 10 substrate sets, which are presented below (Table 2). The reactions for aliphatic systems were performed using 1-5 mol % of copper and 1-10 mol % of AMTC, whereas for aliphatic-aromatic systems, the reactions were performed in 30° C., with 1 mol % of copper and AMTC. After the reaction, ethanol was removed under reduced pressure and the residue was diluted with water and extracted with dichloromethane, washed, dried over $MgSO_4$ and evaporated to obtain the product. The reaction times, amounts of copper and AMTC as well as solvent proportions were selected in Table 2. Below, an example optimal procedure for 1-cyclohexyl-4-(1-hydroxycyclohexylo)-1,2,3-triazole is presented.

It is possible to develop an example using another source of Cu(I) ions —CuBr.

Optimal Procedure

To 0.05 mol/dm$^3$ aqueous solution of CuSO$_4$ (1.4 ml), AMTC (32 mg) was added, dissolved in water (3.3 ml). Next, cyclohexyl azide (0.304 ml) and 3-butyn-2-ol (0.197 ml) were added, followed by ethanol (2.4 ml). The reaction was initiated by slowly adding sodium ascorbate (14 mg), dissolved in water (0.1 ml). The reaction mixture was stirred vigorously for 1.5 h at room temperature. After that time, ethanol was evaporated under reduced pressure and the residue was diluted by adding water (20 ml), and extracted with dichloromethane (3×15 ml; NaCl was added to break the suspension). The combined organic layers were dried over anhydrous MgSO$_4$ and evaporated under reduced pressure. The desired product was obtained as a clear oil (461 mg, 99%), which crystallized to form a greenish solid upon cooling. Identity and purity of the product were examined using NMR and LC-MS analyses.

TABLE 2

Optimal synthetic procedures using AMTC for 10 substrate sets

| Entry. | azide | alkyne | Catalytic system | Time [h] | Isolated yield [%] | HPLC purity [%] | Water/ethanol |
|---|---|---|---|---|---|---|---|
| 1 | trans-2-azidocyclohexanol | H$_3$C-(CH$_2$)$_4$-C≡CH | 10 mol % AMTC, 5 mol % Cu | 2.5 | 82 | 96.5 | 2:1 |
| 2 | trans-2-azidocyclohexanol | H$_3$C-(CH$_2$)$_5$-C≡CH | 2 mol % AMTC, 1 mol % Cu | 24 | 77 | 97.8 | 2:1 |
| 3 | 3-azido-dihydrofuran-2(3H)-one | H$_3$C-(CH$_2$)$_4$-C≡CH | 6 mol % AMTC, 3 mol % Cu | 1 | 89 | 96.7 | 2:1 |
| 4 | 3-azido-dihydrofuran-2(3H)-one | H$_3$C-(CH$_2$)$_5$-C≡CH | 6 mol % AMTC, 3 mol % Cu | 1 | 82 | 94.9 | 2:1 |
| 5 | cyclohexyl azide | HO-CH$_2$-C≡CH | 3 mol % AMTC, 3 mol % Cu | 18 | 75 | 100.0 | 1:2 |
| 6 | cyclohexyl azide | HO-CH(CH$_3$)-C≡CH | 6 mol % AMTC, 3 mol % Cu | 1.5 | 99 | 97.3 | 2:1 |
| 7 | 3-azido-dihydrofuran-2(3H)-one | Ph-C≡CH | 6 mol % AMTC, 3 mol % Cu | 24 | 69 | 95.7 | 2:1 |
| 8 | trans-2-azidocyclohexanol | Ph-C≡CH | 1 mol % AMTC, 1 mol % Cu | 24 | 82 | 100.0 | 2:1 |

TABLE 2-continued

Optimal synthetic procedures using AMTC for 10 substrate sets

| Entry. | azide | alkyne | Catalytic system | Time [h] | Isolated yield [%] | HPLC purity [%] | Water/ethanol |
|---|---|---|---|---|---|---|---|
| 9 | benzyl azide | H₃C−(CH₂)₄−C≡CH | 1 mol % AMTC, 1 mol % Cu | 24 | 95 | 95.1 | 2:1 |
| 10 | benzyl azide | H₃C−(CH₂)₅−C≡CH | 1 mol % AMTC, 1 mol % Cu | 24 | 91 | 96.4 | 2:1 | b. Analysis of AMTC Efficacy and Substrate Selectivity in Comparison to TBTA, THPTA and Ligand-Free Conditions To investigate the substrate selectivity of AMTC and to compare its efficacy to the known ligands—TBTA and THPTA as well as ligand-free conditions, a synthetic protocol was selected using 1 mol % of copper sulphate and sodium ascorbate in 2:1 water:ethanol mixture. The reactions proceeded for 24 h at 30° C., on a 100 mg scale. After the reaction was completed, ethanol was evaporated under reduced pressure and the residue was diluted with water and extracted with dichloromethane. The combined organic layers were washed with 5% aqueous HCl (for efficient ligand removal) and twice with water, dried over anhydrous MgSO₄ and evaporated under reduced pressure. Thus obtained product was weighed and analyzed by LC-MS.

The following procedure was performed for 11 substrate sets: to the 10 substrate sets mentioned above, the reaction of benzyl azide with phenylacetylene (Entry 0 in Table 2), being a "gold standard" for catalytic ligand efficacy testing. The results are collected in FIG. 2, which presents percent increases in cycloaddition yields relative to a ligand-free procedure.

For the substrate sets tested, the use of AMTC allowed to increase the reaction yield and product purity compared to ligand-free procedures. The best results were obtained for aliphatic substrate sets, especially those containing α-azidobutyrolactone (entries 3, 4 as well as 7 in the aliphatic-aromatic part), being the most polar of the azides used. The second group of substrate sets, for which high yields and product purities were obtained were the aliphatic-aromatic substrate sets.

TBTA proved to be more efficient than AMTC only in three cases: for the reaction of benzyl azide with phenylacetylene (Entry 0, the only "purely" aromatic one) and for reactions using propargyl and 3-methylpropargyl alcohols (entries 5 and 6). However, it should be remarked that for the two latter entries the 2:1 water:ethanol solvent system was not optimal, which was shown by the solvent studies described further (EXAMPLE 7 c.).

THPTA gave better results than AMTC also in three cases: for entries 1, 5 and 7; for entry 6 the results for those two ligands were comparable. It needs to be noted that THPTA remained efficient for polar or relatively small substrates, and its efficacy considerably deteriorated with increasing alkyl chain length and decreasing polarity of the substrates, whereas AMTC remained efficient for these systems.

c. Solvent Composition Studies

Based on the presented results, four substrate sets were selected (entries 1, 2, 5, 6) and for them, cycloaddition reactions were performed in water and water-ethanol mixtures of the following compositions: 2:1, 1:2 and 1:9. The reactions were performed according to the same procedure as the one presented above, using 2 mol % of AMTC for entries 1 and 2, and 1 mol % of AMTC for entries 5, 6.

For entries 1 and 2, better results were obtained in water or the 2:1 water:ethanol mixture. It is noteworthy that better product purity was obtained using the ethanol-containing mixture.

Figure 3:
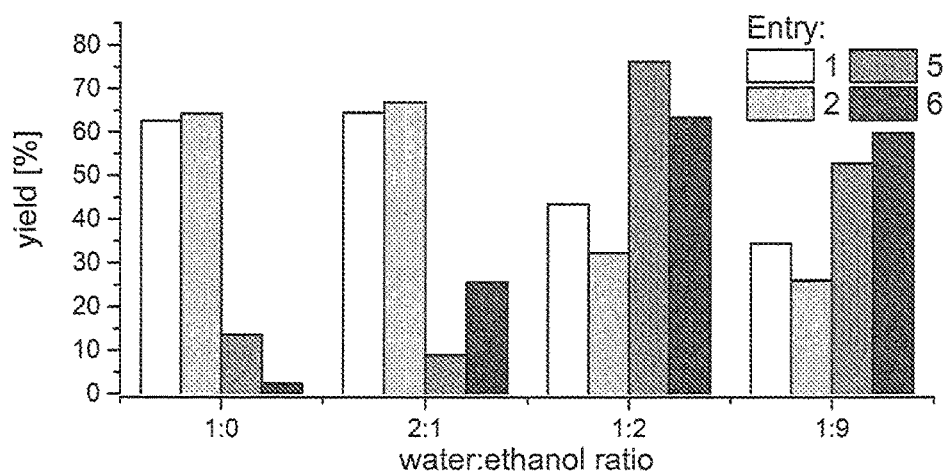
FIG. 3 is a compilation of HPLC yields for the cycloaddition reactions performed in water and water-ethanol mixtures of the following compositions: 2:1, 1:2 and 1:9.

For entries 5 and 6, the differences in yields were considerably larger and the reaction was more efficient in ethanol-rich mixtures (1:2 and 1:9). Higher purity was observed in the 1:2 water:ethanol mixture. A compilation of HPLC yields for the reactions is presented in FIG. 3.

Example 8. Spectral Data for n-Heterocyclic AMTC Analogs

2-{4-[(1H-imidazol-1-yl)methyl]-1H-1,2,3-triazol-1-yl}cyclohexan-1-ol (IMTC)

$^1$H NMR (300 MHz, DEUTERIUM OXIDE) δ ppm 1.00-1.41 (m, 4H) 1.48-1.79 (m, 3H) 1.80-2.06 (m, 3H) 3.70-3.85 (m, 1H) 4.13-4.28 (m, 1H) 5.24 (s, 2H) 6.92 (br. s., 1H) 7.06 (s, 1H) 7.92 (s, 1H)

1-cyclohexyl-4-[(1H-imidazol-1-yl)methyl]-1H-1,2,3-triazol (IMTH)

$^1$H NMR (300 MHz, CHLOROFORM-d) δ ppm 1.12-1.30 (m, 1H) 1.30-1.49 (m, 3H) 1.56-1.76 (m, 3H) 1.86 (dt, J=13.42, 2.95 Hz, 2H) 2.06-2.19 (m, 2H) 4.36 (tt, J=11.72, 3.84 Hz, 1H) 5.20 (s, 2H) 7.01 (d, J=11.83 Hz, 1H) 7.37 (s, 1H) 7.57 (br. s., 1H)

2-{4-[(piperidin-1-yl)methyl]-1H-1,2,3-triazol-1-yl}cyclohexan-1-ol (PPTC)

$^1$H NMR (300 MHz, CHLOROFORM-d) δ ppm 1.07-1.60 (m, 6H) 1.63-2.24 (m, 8H) 2.27-2.54 (m, 4H) 3.58 (s, 2H) 3.89-4.02 (m, 1H) 4.06-4.20 (m, 1H) 7.55 (s, 1H)

(1-[(1-cycloohexyl-1H-1,2,3-triazol-4-yl)methyl]
piperidine (PPTH)

$^1$H NMR (300 MHz, CHLOROFORM-d) δ ppm 1.18-
1.81 (m, 12H) 1.91 (dt, J=13.44, 3.15 Hz, 2H) 2.13-2.26 (m,
2H) 2.34-2.55 (m, 4H) 2.46-2.46 (m, 1H) 3.58-3.65 (m, 2H)
4.42 (tt, J=11.74, 3.86 Hz, 1H) 7.47 (s, 1H)

2-{4-[(piperidin-1-yl)methyl]-1H-1,2,3-triazol-1-
yl}cyclopentan-1-ol (PPTP)

$^1$H NMR (300 MHz, CHLOROFORM-d) δ ppm 1.33-
2.25 (m, 12H) 2.27-2.53 (m, 6H) 3.62 (s, 1H) 4.42-4.62 (m,
2H) 7.55 (s, 1H)

Example 9. Comparison of Catalytic Efficiency of
AMTC and its Analogs

Figure 2:
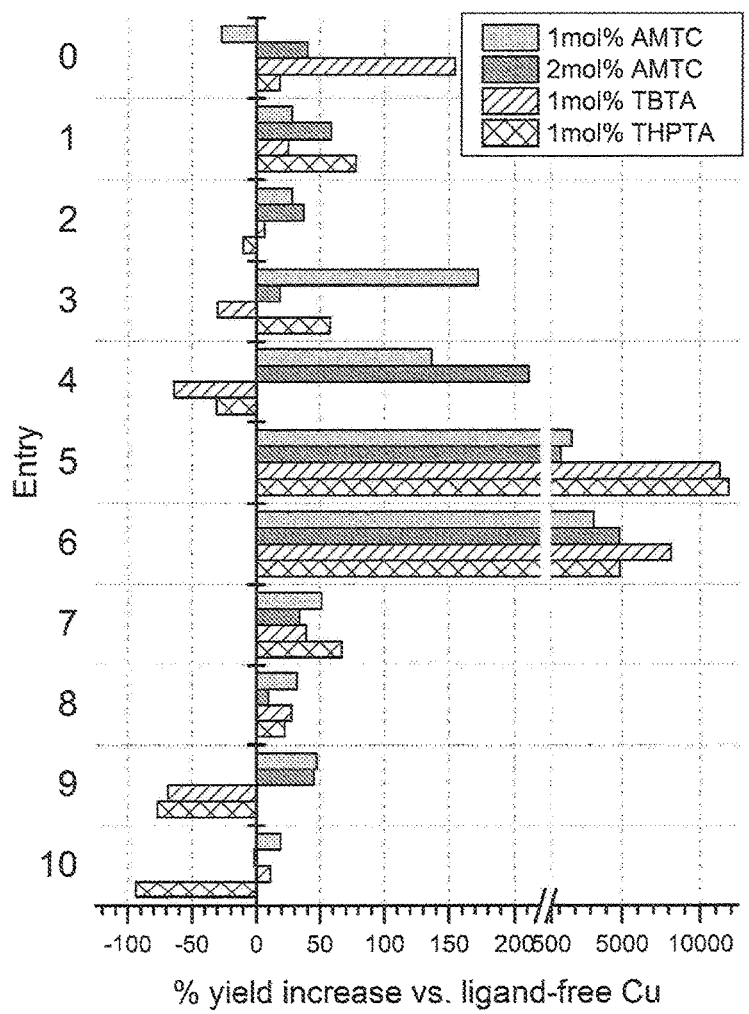
FIG. 2 is a graph of the results collected for catalytic ligand efficacy testing, providing percent increases in cycloaddtion yields relative to a ligand-free procedure.

To compare the catalytic efficiency of a short series of
AMTC analogs, from the previously investigated substrate
sets, one set was chosen, for which the application of a
catalytic ligand markedly improved the yield—the reaction
between but-1-yn-3-ol and azidocyclohexane (Entry 6 in
FIG. 2). This reaction was conducted in small scale for
AMTC and its analogs listed in Example 8 as well as
THPTA, according to the following procedure:

To 3 mL of ethanol, placed in a test tube thermostated in
a water bath at 30° C., 30 µL of azidocyclohexane and 20 µL
but-1-yn-3-ol, followed by 50 µL of 0.05 M CuSO$_4$ and 100
µL of 0.05 mol/dm$^3$ solution of the examined ligand in
ethanol. After the reagents were added, the reaction mixture
was diluted by adding 1.44 mL of water and the reaction was
started by adding 50 µL of 10 mg/mL aqueous sodium
ascorbate. The reaction was stirred in capped tubes thermo-
stated at 30° C. for 18 h. After that time it was quenched by
adding 50 µL of 3% aqueous hydrogen peroxide and 500 µL
sample was taken, diluted 10 times with HPLC-grade
acetonitrile and analyzed by HPLC. The reaction yields were
estimated by comparing the peak area for the 1,2,3-triazole
product obtained in the reaction and the area obtained for a
reaction mixture prepared in the way described above, but
containing the product in a quantity corresponding to 100%
yield instead of the substrates (46 mg).

Figure 4:
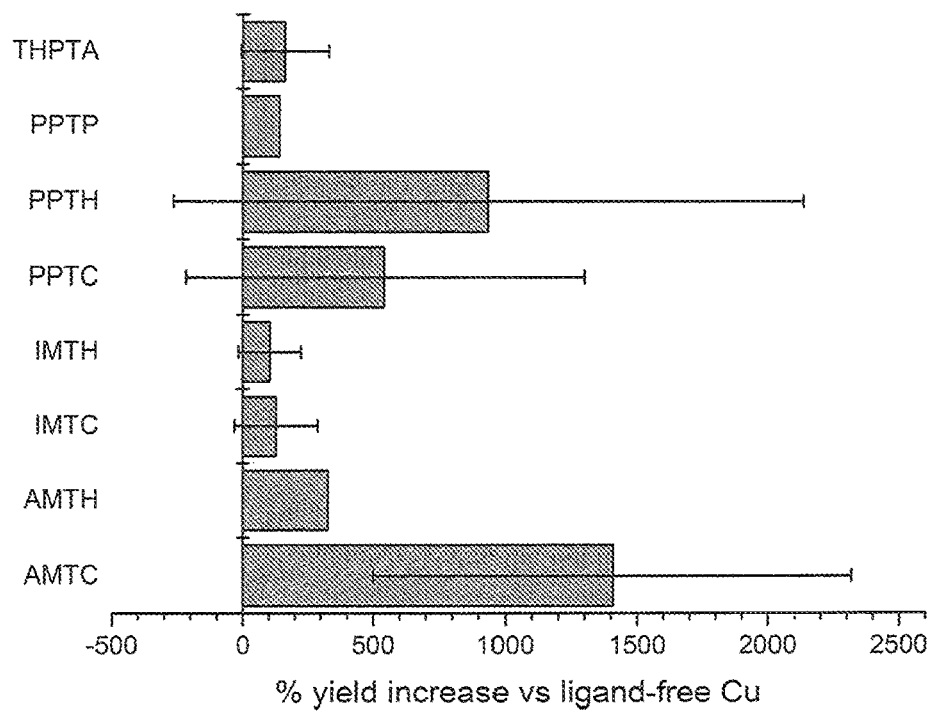
FIG. 4 is graph of the reactions performed for AMTH, AMTH, IMTH, IMTC, PPTC, PPTH, PPTP, THPTA and a ligand-free system, wherein, from the results, the % yield increase was calculated and plotted.

The reactions according to this protocol were performed
for AMTH, AMTH, IMTH, IMTC, PPTC, PPTH, PPTP,
THPTA and a ligand-free system. From the results, the %
yield increase was calculated (as in the earlier examples) and
plotted in FIG. 4. The highest yield obtained for systems
comprising tertiary aliphatic amine. For the rest of systems
less significant, however still clear increase of yield of
reaction was observed.

LITERATURE REFERENCES

[1] A. Michael, No Title, *J. Für Prakt. Chemie.* 48 (1893)
94-95.
[2] R. Huisgen, *Kinetics and Mechanism of 1,3-Dipolr
Cycloadditions, Angew. Chemie Int. Ed. English.* 2 (1963)
633-645. doi:10. 1002/anie.196306331.
[3] R. Huisgen, *1,3-Dipolar Cycloadditions. Past and
Future, Angew. Chemie Int. Ed. English.* 2 (1963) 565-
598. doi:10.1002/anie.196305651.
[4] HC. Kolb, M. G. Finn, K. B. Sharpless, *Click Chemistry:
Diverse Chemical Function from a Few Good Reactions.,
Angew. Chem. Int. Ed. Engl.* 40 (2001) 2004-2021. http://
www.ncbi.nlm.nih.gov/pubmed/11433435 (accessed Apr.
28, 2014).
[5] C. Tornoe, M. Meldal, *Peptidotriazoles: Copper (I)-
catalyzed 1, 3-dipolar cycloadditions on solid-phase, in:
Pept. Wave Futur. Proc. Second Int. Seventeenth Am.
Pept. Symp.* Jun. 9-14, 2001, San Diego, Calif., U.S.A.,
2001. pp. 3057-3064. http://link.springer.com/chapter/1
0.1007/978-94-010-0464-0_119 (accessed Dec. 30,
2014).
[6] V V. Rostovtsev, L. G. Green, V. V. Fokin, K. B.
Sharpless, *A Stepwise Huisgen Cycloaddition Process.
Copper(I)-Catalyzed Regioselective "Ligation" of Azides
and Terminal Alkynes, Angew. Chemie.* 114 (2002) 2708-
2711. doi:10.1002/1521-3757(20020715)114:14<2708:
AID-ANGE2 708>3.0. CO; 2-0.
[7] M. Meldal, C. W. Tornoe, *Cu-catalyzed azide-alkyne
cycloaddition., Chem. Rev.* 108 (2008) 2952-3015. doi:
10.1021/cr0783479.
[8] L. Zhang, X. Chen, P. Xue, H H Y. Sun, I. D. Williams,
K. B. Sharpless, et al., *Ruthenium-catalyzed cycloaddition
of alkynes and organic azides., J. Am. Chem. Soc.* 127
(2005) 15998-9. doi:10.1021/ja054114s.
[9] B. C. Boren, S. Narayan, L. K. Rasmussen, L. Zhang, H.
Zhao, Z. Lin, et al., *Ruthenium-catalyzed azide-alkyne
cycloaddition: scope and mechanism., J. Am. Chem. Soc.*
130 (2008) 8923-30. doi:10.1021/ja0749993.
[10] J. H. M. Lange, C. G. Kruse, *Keynote review: Medicinal
chemistry strategies to CB1 cannabinoid receptor antago-
nists., Drug Discov. Today.* 10 (2005) 693-702. doi:
10.1016/S1359-6446(05)03427-6.
[11] G. C. Tron, T. Pirali, R. A. Billington, P. L. Canonico,
G. Sorba, A. A. Genazzani, *Click chemistry reactions in
medicinal chemistry: applications of the 1,3-dipolar
cycloaddition between azides and alkynes., Med. Res.
Rev.* 28 (2008) 278-308. doi.10.1002/med.20107.
[12] H. C. Kolb, K B. Sharpless, *The growing impact of click
chemistry on drug discovery, Drug Discov. Today.* 8
(2003) 1128-1137. doi:10.1016/S1359-6446(03)02933-7.
[13] C. D. Hein, X-M. Liu, D. Wang, *Click chemistry, a
powerful tool for pharmaceutical sciences., Pharm. Res.*
25 (2008) 2216-30. doi:10.1007/s11095-008-9616-1.
[14] P. Thirumurugan, D. Matosiuk, K. Jozwiak, *Click
chemistry for drug development and diverse chemical-
biology applications., Chem. Rev.* 113 (2013) 4905-79.
doi:10.1021/cr200409f.
[15] W. H. Binder, R. Sachsenhofer, *"Click" Chemistry in
Polymer and Materials Science, Macromol. Rapid Com-
mun.* 28 (2007) 15-54. doi: 10.1002/marc.200600625.
[16] W. Binder, R. Sachsenhofer, *"Click" chemistry in
polymer and material science: an update, Macromol.
Rapid Commun.* 29 (2008) 952-981. http://onlinelibrary-
.wiley.com/doi/10.1002/marc.200800089/full (accessed
Dec. 30, 2014).
[17] C. W. Tornoe, C. Christensen, M. Meldal, *Peptidotri-
azoles on Solid Phase: [1,2,3]-Triazoles by Regiospecific
Copper(I)-Catalyzed 1,3-Dipolar Cycloadditions of Ter-
minal Alkynes to Azides, J. Org. Chem.* 67 (2002) 3057-
3064. doi:10.1021/jo011148j.
[18] V. D. Bock, H. Hiemstra, J. H. van Maarseveen,
*CuI-Catalyzed Alkyne-Azide "Click" Cycloadditions
from a Mechanistic and Synthetic Perspective, European
J. Org. Chem.* 2006 (2006) 51-68. doi: 10.1002/
ejoc.200500483.
[19] J. E. Hein, V. V Fokin, *Copper-catalyzed azide-alkyne
cycloaddition (CuAAC) and beyond: new reactivity of
copper(I) acetylides., Chem. Soc. Rev.* 39 (2010) 1302-
1315. doi10.1039/b904091a.

[20] R. G. Pearson, Electronic spectra and chemical reactivity, J. Am. Chem. Soc. 110 (1988) 2092-2097. doi: 10.1021/ja00215a013.
[21] F. Hathaway, No Title, 1987.
[22] F. Pérez-Balderas, M. Ortega-Muñoz, J. Morales-Sanfrutos, F. Herndández-Mateo, F. G. Calvo-Flores, J. a. Calvo-Asin, et al., *Multivalent neoglycoconjugates by regiospecific cycloaddition of alkynes and azides using organic-soluble copper catalysts*, Org. Lett. 5 (2003) 1951-1954. doi.10.1021/o1034534r.
[23] M. Malkoch, K. Schleicher, E. Drockenmuller, C. J. Hawker, T. P. Russell, P. Wu, et al., *Structurally Diverse Dendritic Libraries:  A Highly Efficient Functionalization Approach Using Click Chemistry*, Macromolecules. 38 (2005) 3663-3678. doi: doi:10.1021/ma047657f.
[24] P. Wu, A. K. Feldman, A. K. Nugent, C. J. Hawker, A. Scheel, B. Voit, et al., *Efficiency and fidelity in a click-chemistry route to triazole dendrimers by the copper(I)-catalyzed ligation of azides and alkynes*, Angew. Chemie—Int. Ed. 43 (2004) 3928-3932. doi:10.1002/anie.200454078.
[25] Z. Gonda, Z. Novdk, *Highly active copper-catalysts for azide-alkyne cycloaddition.*, Dalton Trans. 39 (2010) 726-729. doi.10.1039/b920790m.
[26] H. Kaur, F. K. Zinn, E. D. Stevens, S. P. Nolan, *(NHC) CuI (NHC=N-Heterocyclic carbene) complexes as efficient catalysts for the reduction of carbonyl compounds*, Organometallics. 23 (2004) 1157-1160. doi:10.1021/om034285a.
[27] S. Díez-Gonzlez, S. P. Nolan, *[(NHC)2Cu]X complexes as efficient catalysts for azide-alkyne click chemistry at low catalyst loadings*, Angew. Chemie—Int. Ed. 47 (2008) 8881-8884. doi.10.1002/anie.200803289.
[28] S. Diez-González, A. Correa, L. Cavallo, S. P. Nolan, *(NHC)copper(I)-catalyzed [3+2]cycloaddition of azides and Mono- Or disubstituted alkynes*, Chem.—A Eur. J. 12 (2006) 7558-7564. doi: 10.1002/chem.200600961.
[29] S. Diez-González, *Well-defined copper(i) complexes for Click azide-alkyne cycloaddition reactions: one Click beyond*, Catal. Sci. Technol. 1 (2011) 166. doi:10.1039/c0cy00064 g.
[30] S. Diez-González, E. D. Stevens, S. P. Nolan, *A [(NHC)CuCl] complex as a latent Click catalyst.*, Chem. Commun. (Camb). (2008) 4747-4749. doi: 10.1039/b806806b.
[31] P. L. Golas, N. V Tsarevsky, B. S. Sumerlin, K. Matyjaszewski, *Catalyst Performance in “ Click” Coupling Reactions of Polymers Prepared by ATRP:  Ligand and Metal Effects*, Macromolecules. 39 (2006) 6451-6457. doi: doi: 10.1021/ma061592u.
[32] T. R. Chan, R. Hilgraf K. B. Sharpless, V V Fokin, *Polytriazoles as copper(I)-stabilizing ligands in catalysis.*, Org. Lett. 6 (2004) 2853-5. doi:10.1021/ol10493094.
[33] S. Özçubukçu, E. Ozkal, C. Jimeno, M A. Pericàs, *A highly active catalyst for Huisgen 1,3-dipolar cycloadditions based on the tris(triazolyl)methanol-Cu(I) structure.*, Org. Lett. 11 (2009) 4680-3. doi:10.1021/o19018776.
[34] E. Ozkal, S. Özçubukçu, C. Jimeno, M A. Pericàs, *Covalently immobilized tris(triazolyl)methanol-Cu(i) complexes: highly active and recyclable catalysts for CuAAC reactions*, Catal. Sci. Technol. 2 (2012) 195. doi: 10.1039/c1cy00297j.
[35] H. Hiroki, K. Ogata, S. Fukuzawa, *2-Ethynylpyridine-Promoted Rapid Copper(I) Chloride Catalyzed Azide-Alkyne Cycloaddition Reaction in Water*, Synlett. 24 (2013) 843-846. doi. 10.1055/s-0032-1318488.

The invention claimed is:

1. The compound of the general formula:

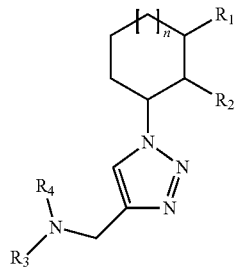

wherein:

substituents in the aliphatic ring are in cis- or trans- relative configuration, and $R_1$ is one of the following substituents: —H, =O, —OH, —OCH$_3$, —NH$_2$, —N(CH$_3$)$_2$, —NHCH$_3$ —SH, or —SCH$_3$ $R_2$ is one of the following substituents: —H, =O, —OH, —OCH$_3$, —NH$_2$, —N(CH$_3$)$_2$, —NHCH$_3$ —SH, or —SCH$_3$ n is an integer from 0 to 3

$R_3$ is an alkyl chain containing 1-3 carbon atoms, $R_4$ is an alkyl chain containing 1-3 carbon atoms, or substituents in the aliphatic ring are in cis- or trans- relative configuration, and $R_1$ is one of the following substituents: —H, =O, —OH, —OCH$_3$, —NH$_2$, —N(CH$_3$)$_2$, —NHCH$_3$ —SH, or —SCH$_3$ $R_2$ is one of the following substituents: —H, =O, —OH, —OCH$_3$, —NH$_2$, —N(CH$_3$)$_2$, —NHCH$_3$ —SH, or —SCH$_3$ n is an integer from 0 to 3 and $R_3$ and $R_4$ together with the nitrogen atom form one of the systems presented below:

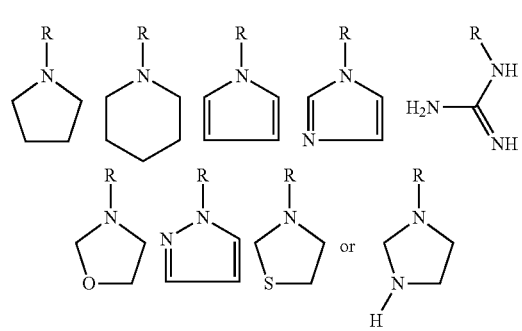

wherein R is the remaining part of the molecule described above.

2. The compound according to claim 1, wherein the structure is the following formula:

17

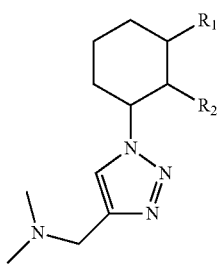

wherein R₁ is hydrogen and R₂ is a hydroxyl group in trans-position or R₂ is hydrogen and R₁—a hydroxyl group in any relative configuration, or R₁ and R₂ are hydrogen atoms.

3. The compound according to claim 1, wherein the structure is the following formula:

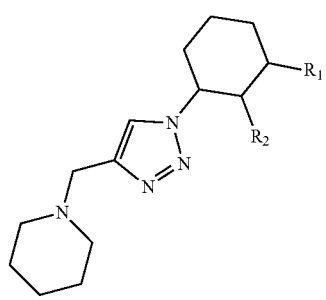

wherein R₁ is hydrogen and R₂ is a hydroxyl group in trans-position or R₂ is hydrogen and R₁—a hydroxyl group in any relative configuration, or R₁ and R₂ are hydrogen atoms.

4. The compound according to claim 1, which is 2-{4-[(dimethylamine)methyl]-1,2,3-triazolyl}cyclohexan-1-ol.

5. A method for accelerating a copper(I)-catalyzed azide—alkyne cycloaddition reaction comprising:
using a compound of the general formula:

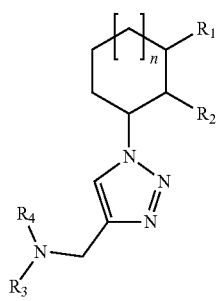

wherein:
substituents in the aliphatic ring are in cis- or trans-relative configuration, and
R₁ is one of the following substituents: —H, =O, —OH, —OCH3, —NH2, —N(CH3¬)2, —NHCH3 or —SCH3
R₂ is one of the following substituents: —H, =O, —OH, —OCH3, —NH2, —N(CH3¬)2, —NHCH3 —SH, or —SCH3
n is an integer from 0 to 3
R₃ is an alkyl chain containing 1-3 carbon atoms,

18

R₄ is an alkyl chain containing 1-3 carbon atoms, or
substituents in the aliphatic ring are in cis- or trans-relative configuration, and
R₁ is one of the following substituents: —H, =O, —OH, —OCH3, —NH2, —N(CH3¬)2, —NHCH3 —SH, or —SCH3
R₂ is one of the following substituents: —H, =O, —OH, —OCH3, —NH2, —N(CH3¬)2, —NHCH3 —SH, or —SCH3
n is an integer from 0 to 3
and R₃ and R₄ together with the nitrogen atom form one of the systems presented below:

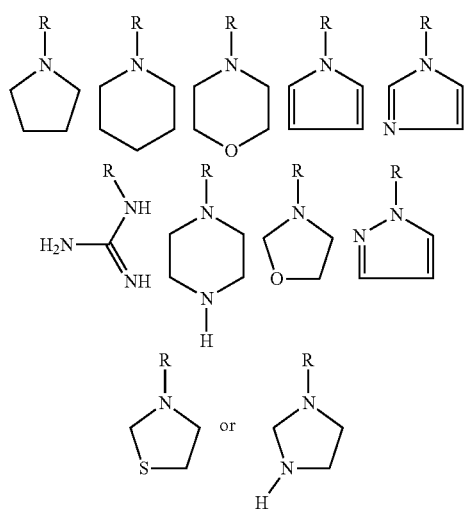

wherein R is the remaining part of the molecule described above, as a ligand in the cycloaddition reaction.

6. A method for accelerating a zinc(II)-catalyzed azide—nitrile cycloaddition reaction comprising:
using a compound of the general formula:

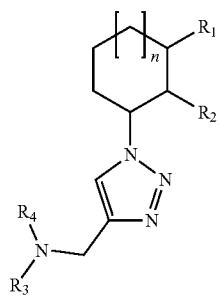

wherein:
substituents in the aliphatic ring are in cis- or trans-relative configuration, and
R₁ is one of the following substituents: —H, =O, —OH, —OCH3, —NH2, —N(CH3¬)2, —NHCH3 —SH, or —SCH3
R₂ is one of the following substituents: —H, =O, —OH, —OCH3, —NH2, —N(CH3¬)2, —NHCH3 —SH, or —SCH3
n is an integer from 0 to 3
R₃ is an alkyl chain containing 1-3 carbon atoms,
R₄ is an alkyl chain containing 1-3 carbon atoms, or substituents in the aliphatic ring are in cis- or trans-relative configuration, and R₁ is one of the following substituents: —H, =O, —OH, —OCH3, —NH2, —N(CH3¬)2, —NHCH3 —SH, or —SCH3

R₂ is one of the following substituents: —H, =O, —OH, —OCH3, —NH2, —N(CH3¬)2, —NHCH3 —SH, or —SCH3 n is an integer from 0 to 3 and R₃ and R₄ together with the nitrogen atom form one of the systems presented below:

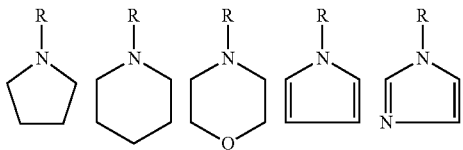

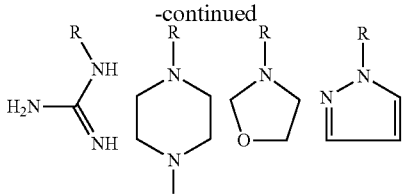

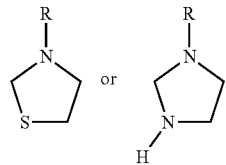

wherein R is the remaining part of the molecule described above, as a ligand in the cycloaddition reaction.

* * * * *